(12) United States Patent
Reeves et al.

(10) Patent No.: US 8,076,476 B2
(45) Date of Patent: Dec. 13, 2011

(54) SYNTHESIS OF MORPHOLINO OLIGOMERS USING DOUBLY PROTECTED GUANINE MORPHOLINO SUBUNITS

(75) Inventors: Matthew Dale Reeves, Albany, OR (US); Dwight D. Weller, Corvallis, OR (US); Yongfu Li, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 263 days.

(21) Appl. No.: 12/271,040

(22) Filed: Nov. 14, 2008

(65) Prior Publication Data

US 2009/0131624 A1 May 21, 2009

Related U.S. Application Data

(60) Provisional application No. 60/988,200, filed on Nov. 15, 2007.

(51) Int. Cl.
  *C07D 413/04* (2006.01)
  *C07D 413/14* (2006.01)
(52) U.S. Cl. ..................................... 544/118
(58) Field of Classification Search .................. 544/118
  See application file for complete search history.

(56) References Cited

U.S. PATENT DOCUMENTS

| 5,185,444 A | 2/1993 | Summerton et al. | |
|---|---|---|---|
| 2007/0135333 A1 | 6/2007 | Geller et al. | |
| 2008/0194463 A1* | 8/2008 | Weller et al. | 514/7 |
| 2009/0088562 A1* | 4/2009 | Weller et al. | 536/24.5 |
| 2010/0234281 A1* | 9/2010 | Weller et al. | 514/8 |

FOREIGN PATENT DOCUMENTS

| WO | WO98/17281 A1 | 4/1998 |
|---|---|---|
| WO | WO 2008/008113 A1 * | 1/2008 |
| WO | WO 2008/036127 A1 * | 3/2008 |

OTHER PUBLICATIONS

Gaffney et al., "Synthesis of O-6-Alkylated Deoxyguanosine Nucleosides," *Tetrahedron Letters* 23(22):2253-2256, 1982.
Gaffney et al., "A New Strategy for the Protection of Deoxyguanosine During Oligonucleotide Synthesis," *Tetrahedron Letters* 23(22):2257-2260, 1982.
International Preliminary Report on Patentability for International Application No. PCT/US2008/012804, mailed May 18, 2010, 6 pages.
Jones et al., "The Protection of Uracil and Guanine Residues in Oligonucleotide Synthesis," *Tetrahedron Letters* 22(47):4755-4758, 1981.
Kamimura et al., "Diphenylcarbamoyl and Propionyl Groups: A New Combination of Protecting Groups for the Guanine Residue," *Tetrahedron Letters* 24(27):2775-2778, 1983.
Mitsunobu, "The Use of Diethyl Azodicarboxylate and Triphenylphosphone in Synthesis and Transformation of Natural Products," *Synthesis* 1:1-28, 1981.

Abramova, T.V. et al., "Synthesis of Morpholine Nucleoside Triphosphates", *Tetrahedron Letters*, 45(22):4361-4364 (2004).
Abramova, T.V. et al., "New Oligonucleotide analogues based on Morpholine Subunits Joined by Oxalyl Diamide Tether", *Bioorgainic Chemistry*, 35:258-275 (2007).
Bodanszky, M. and Bodanszky, A., "Coupling in Absence of Tertiary Amines: III. Deprotection with the Help of the Carboxyl Components or its Activated Derivatives", *Int. J. Peptide Protein Res.*, 26:98-104 (1985).
Castro, M.J. et al., "Gemini Surfactants from Alkyl Glucosides", *Tetrahedron Letters*, 38 (23):3995-3998 (1997).
The International Search Report and Written Opinion for PCT application PCT/US2008/012804, Search Report dated Apr. 7, 2009, 14 pages (2009).
Klostermeyer et al. "Removal of Acid-Labile Amino-Protecting Groups by Pyridinium Salts" *Anorganische Chemie, Organische Chemie, Biochemie, Biophysik, Biologie*, 28(5-6):334-338 (1973). (Abstract Only).
Andrus, M.B., "Total Synthesis if the Hydroxyketone Kurasoin A Using Asymmetric Phase-Transfer Alkylation", *J. Org. Chem.*, 71:8651-8654 (2006).

(Continued)

*Primary Examiner* — Rebecca Anderson
(74) *Attorney, Agent, or Firm* — Seed IP Law Group PLLC

(57) ABSTRACT

Morpholino compounds are provided having the structure:

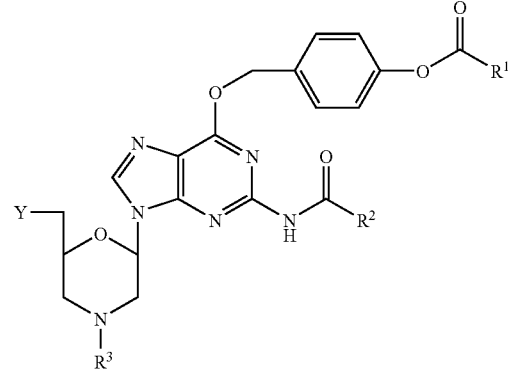

where
  $R^1$ is selected from the group consisting of lower alkyl, di(lower alkyl)amino, and phenyl;
  $R^2$ is selected from the group consisting of lower alkyl, monocyclic arylmethyl, and monocyclic (aryloxy)methyl;
  $R^3$ is selected from the group consisting of triarylmethyl and hydrogen; and
  Y is selected from the group consisting of: a protected or unprotected hydroxyl or amino group; a chlorophosphoramidate group; and a phosphorodiamidate linkage to the ring nitrogen of a further morpholino compound or a morpholino oligomer. Such compounds include doubly protected morpholino guanine (MoG) monomers. Also described is their use in synthesis of morpholino oligomers.

16 Claims, 11 Drawing Sheets

OTHER PUBLICATIONS

Briggs, A.D. et al., "Acyloxymethyl and 4-Acyloxybenzyl Diester Prodrugs if Phospphonoformate" *Tetrahedron*, 52(47):14937-14950 (1996).

Gaffney, B.L. and Jones, R.A. et al., "A New Strategy for the Protection of Deoxyguanosine During Oligonucleotide Synthesis", *Tetrahedron Letters*, 23(22):2257-2260 (1982).

Gaffney, B.L. and Jones, R.A. et al., "Synthesis of O-6-Alkylated Deoxyguanosine Nucleosides", *Tetrahedron Letters*, 23(22):2253-2256 (1982).

Gough et al., "The use of barium salts of protected deoxyribonucleoside-3' p-chlorophenyl phosphates for construction of oligonucleotides by the phosphotriester method: high-yield synthesis of dinucleotide blocks", *Nucleic Acids Research*, 7(37:195551964 (1979).

Himmelsbach, F. et al., "The p-Nitrophenylethyl (NPE) Group, A Versatile New Blocking Group for Phosphate abd Aglycone Protection in Nucleosides and Nucleotides", *Tetrahedron*, 40:59-72 (1984).

Iyer, R. et al., "Bioreversible Oligonucleotide Conjugates by Site-Specific Derivatization", *Bioorganic and Medicinal Chemistry Letters*, 7(7):871-876 (1997).

Jones et al., "The Protection of Uracil and Guanine Residues in Oligonucleotide Synthesis", *Tetrahedron Letters*, 22(7):4755-4758 (1981).

Kamimura, T. et al., "Diphenylcarbamoyl and Propionyl Groups: A New Combination if Protecting Groups for the Guamnine Residue", *Tetrahedron Letters*, 24(27):2775-2778 (1983).

Reese, "The Protection of Thymine and Guanine Residues in Oligodeoxyribonucleotide Synthesis", *J. Chem.Soc., Perkin Trans.* 1, 1263-1270 (1984).

Summerton, J. and Weller, D., "Morpholino antisense oligomers: design, preparation, and properties", *Antisense Nucleic Acid Drug Dev.*, 7(3):187-95 (1997).

Takaku, H. et al., "3,4-Dimethoxybenzyl Group: A New Protecting Group for the Guanosine Residue During Oligonucleotide Synthesis", *Chem Pharm Bull.*, 32(7) 2882-2885 (1984).

* cited by examiner

SYNTHESIS OF MORPHOLINO OLIGOMERS USING DOUBLY PROTECTED GUANINE MORPHOLINO SUBUNITS

This patent application claims priority to U.S. Provisional Patent Application No. 60/988,200 filed Nov. 15, 2007, which is incorporated in its entirety herein by reference.

FIELD OF THE INVENTION

The invention relates to methods of synthesis using guanine morpholino (MoG) subunits with protection at both the N2 and O6/N1 groups of the guanine base. Morpholino oligomers synthesized using these subunits are obtained in higher purity and yield compared to those synthesized using monoprotected guanine subunits.

REFERENCES

Gough et al. (1979) *Nucleic Acids Research* 7:1955-1964.
Hata et al. (1983) *Tetrahedron Lett.* 24:2775-2778.
Jones et al. (1982A) *Tetrahedron Lett.* 23:2253-2256.
Jones et al. (1982B) *Tetrahedron Lett.* 23:2257-2260.
Mitsunobu, O. (1981) *Synthesis* 1:1-28.
Reese et al. (1981) *Tetrahedron Lett.* 22:4755-4758.
Reese et al. (1984) *J. Chem. Soc., Perkin Trans.* 11263-1270.
Summerton, J. E. and Weller, D. D. (1993) U.S. Pat. No. 5,185,444.
Summerton, J. E. and Weller, D. D. (1997) *Antisense Nucl. Acid Drug Dev.* 7(3):187-195.

BACKGROUND

Phosphorodiamidate-linked morpholino oligomers, or PMO, are nucleic acid analogs which bind tightly and sequence specifically to complementary RNA and are useful in modulating protein synthesis and thus gene expression. These oligomers are composed of base-pairing recognition moieties (heterocyclic bases) supported by a morpholino backbone system. Morpholino subunits for use in synthesizing such oligomers can be prepared easily from the corresponding ribonucleosides, which are readily available and inexpensive precursors (see e.g. Summerton and Weller, 1993, 1997).

During such synthesis, as in conventional oligonucleotide synthesis, the functional groups on the heterocyclic bases are typically masked to prevent interference in the synthetic transformations. For example, activation of the N-tritylated morpholino monomer (1a-f; FIG. 1) entails reaction of the 5'-hydroxyl with a suitable phosphoramido dichloridate to form the activated subunit 2a-f. At large scale (50-100 Gallon reactor), the crude activated subunit is generally contaminated with a high level of by-products. Following chromatographic purification, the activated subunit is isolated in about 50% yield for A, C, I, T, U and their protected forms, but only in about 5% yield for the activated singly protected G subunit, which is believed to be due to the presence of the unprotected O6 oxygen.

The O6-unprotected guanine subunit also gives rise to side reactions at the oligomer stage. For example, the O6 oxygen can react with activated subunit during coupling steps, to form O6-phosphorylated or derivative species, and during final cleavage of the base protecting groups with ammonia, ammonia can react at C6 to displace these species, giving a diaminopurine derivative. Such impurities are difficult to remove by chromatography, and cause a large loss in yield.

Various protection schemes have been proposed in the art to reduce side reactions of unprotected guanine O6 positions in conventional oligonucleotide synthesis (see e.g. Gough et al. 1979; Reese et al. 1981, 1984; Jones et al. 1982A, 1982B). However, these protocols were largely unsuccessful when applied to PMO synthesis. Accordingly, improved methods were sought to increase yield and purity in PMO synthesis, particularly in the use of G morpholino subunits.

SUMMARY

In one aspect, the invention provides a morpholino compound comprising the structure I:

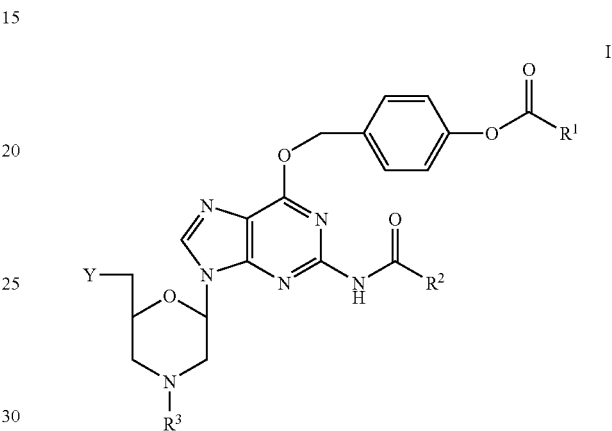

wherein
$R^1$ is selected from the group consisting of lower alkyl, di(lower alkyl)amino, and phenyl;
$R^2$ is selected from the group consisting of lower alkyl, monocyclic arylmethyl, and monocyclic (aryloxy)methyl;
$R^3$ is selected from the group consisting of triarylmethyl and hydrogen; and
Y is selected from the group consisting of: a protected or unprotected hydroxyl or amino group; a chlorophosphoramidate group; and a phosphorodiamidate linkage to the ring nitrogen of a further morpholino compound or a morpholino oligomer.

In selected embodiments, Y is selected from the group consisting of a protected or unprotected hydroxyl group and a chlorophosphoramidate group, e.g. a chlorophosphoramidate group of the form —O—P(=O)—N(CH$_3$)$_2$Cl. When Y is a protected hydroxyl group, it is preferably a trialkylsilyl-protected hydroxyl group.

The group $R^3$ is preferably selected from trityl (triphenylmethyl), 4-methoxytrityl, 4-methyltrityl, 4,4'-dimethyltrityl, and 4,4',4"-trimethyltrityl. The group $R^1$ is preferably lower alkyl, especially $C_1$-$C_4$ alkyl, and most particularly —C(CH$_3$)$_3$ (tert-butyl). The group $R^2$ is preferably selected from benzyl and —CH(CH$_3$)$_2$ (isopropyl).

In a related aspect, the invention provides an improved method of synthesizing a morpholino oligomer, the method comprising:

(a) reacting a solid-phase-supported morpholino subunit, having an unprotected ring nitrogen, with a base-protected morpholino subunit monomer, having a triarylmethyl-protected ring nitrogen and an activated phosphoramidate group on a 5'-exocyclic carbon, thereby forming a phosphorodiamidate linkage between the 5'-exocyclic carbon and the unprotected ring nitrogen;

(b) deprotecting the protected ring nitrogen, to form an unprotected ring nitrogen; and (c) repeating steps (a) and (b) one or more times with further base-protected morpholino subunit monomers;

wherein at least one of the base-protected morpholino subunit monomers is a doubly protected guanine morpholino compound having the structure I:

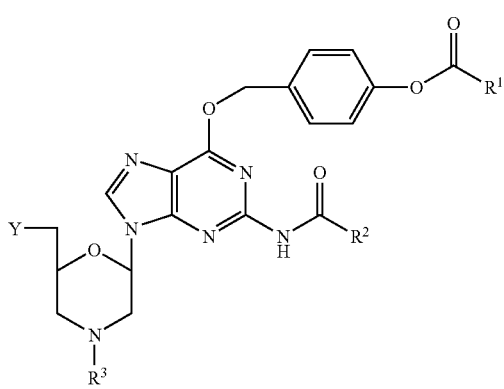

wherein

R¹ is selected from the group consisting of lower alkyl, di(lower alkyl)amino, and phenyl;

R² is selected from the group consisting of lower alkyl, monocyclic arylmethyl, and monocyclic (aryloxy)methyl;

R³ is selected from the group consisting of triarylmethyl and hydrogen; and

Y is a chlorophosphoramidate group.

Selected embodiments of the variables represented in the above structure include those described above.

These and other objects and features of the invention will become more fully apparent when the following detailed description of the invention is read in conjunction with the accompanying drawings.

DETAILED DESCRIPTION OF THE INVENTION

I. Definitions

Figure 1:
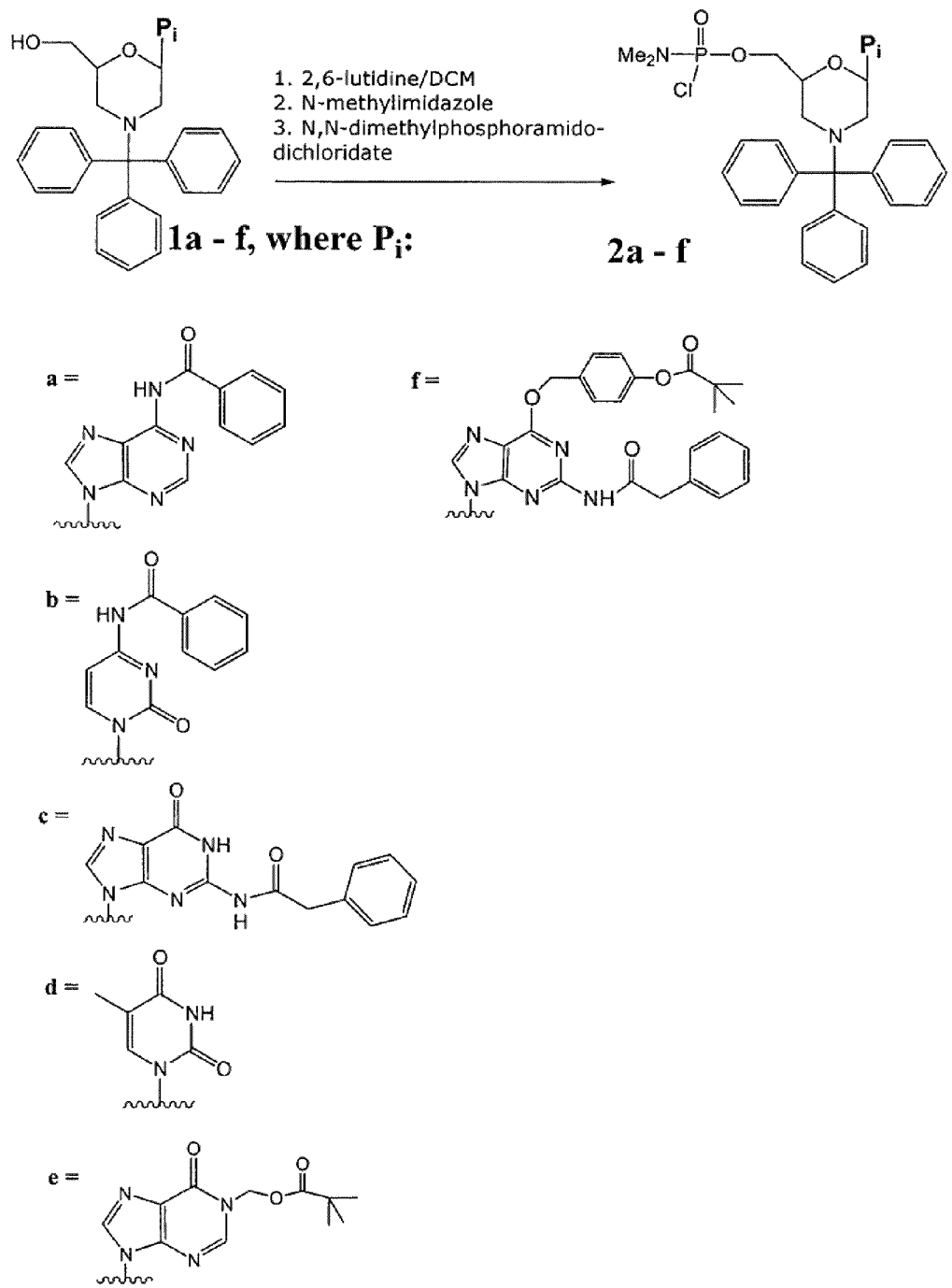
FIG. 1 illustrates the formation of an activated morpholino subunit.

The terms below, as used herein, have the following meanings, unless indicated otherwise:

A "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred morpholino oligomer is composed of "morpholino subunit" structures, such as shown below, which in the oligomer are preferably linked together by (thio)phosphorodiamidate linkages, joining the morpholino nitrogen of one subunit to the 5' exocyclic carbon of an adjacent subunit. Each subunit includes a purine or pyrimidine base-pairing moiety Pi which is effective to bind, by base-specific hydrogen bonding, to a base in a polynucleotide.

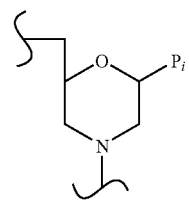

Morpholino oligomers are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

A "phosphorodiamidate" group comprises phosphorus having two attached oxygen atoms and two attached nitrogen atoms, and herein may also refer to phosphorus having one attached oxygen atom and three attached nitrogen atoms. In the intersubunit linkages of the oligomers described herein, one nitrogen is typically pendant to the backbone chain, and the second nitrogen is the ring nitrogen in a morpholino ring structure, as shown in formula II below. Alternatively or in addition, a nitrogen may be present at the 5'-exocyclic carbon, as shown in formulas III and IV below.

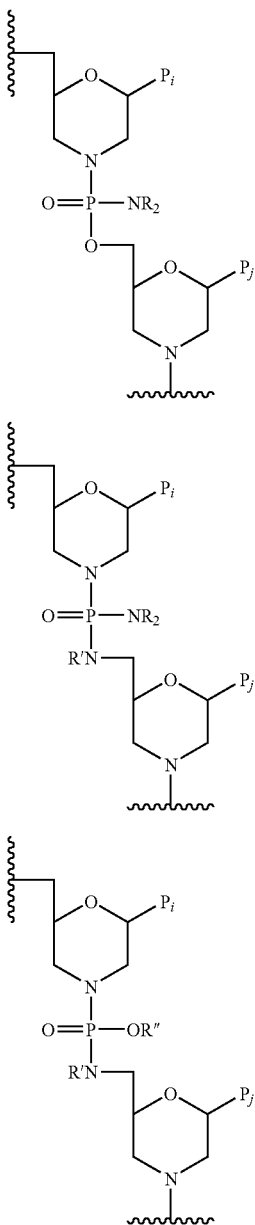

In a thiophosphorodiamidate linkage, one oxygen atom, typically an oxygen pendant to the backbone in the oligomers described herein, is replaced with sulfur.

A "solid-phase-supported morpholino subunit" can be the first or any subsequent morpholino subunit monomer incorporated into a morpholino oligomer by solid-phase stepwise synthesis as described herein. The subunit is attached to the solid support, or to a growing oligomer chain on the solid support, via its 5' exocyclic carbon. "Base-protected" refers to protection of the base-pairing groups, e.g. purine or pyrimidine bases, on the morpholino subunits with protecting groups suitable to prevent reaction or interference of the base-pairing groups during stepwise oligomer synthesis.

An "activated phosphoramidate group" is typically a chlorophosphoramidate group, having substitution at nitrogen which is desired in the eventual phosphoramidate linkage in the oligomer. An example is (dimethylamino)chlorophosphoramidate, i.e. —O—P(=O)(NMe$_2$)Cl.

The terms "charged", "uncharged", "cationic" and "anionic" as used herein refer to the predominant state of a chemical moiety at near-neutral pH, e.g. about 6 to 8. Preferably, the term refers to the predominant state of the chemical moiety at physiological pH, i.e. about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms, or 1-2 carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and preferably non-polar groups such as methyl, ethyl, methoxy, ethoxy, hydroxy, or fluoro.

II. Base Protection in PMO Synthesis

Due to the specific challenges of the morpholino chemistry, a base protecting group must fill several requirements. The protecting group should be readily introduced onto the heterocyclic moiety and thereafter be stable to subunit activation and purification conditions, and solid phase synthesis. The protecting group should not be reactive with the morpholino amine moiety of the growing chain, and should allow the activated morpholino subunit to couple cleanly with the growing oligomer chain. The protecting group should be cleaved, preferably by ammonia, without introducing new impurities. Finally, it should result in crystalline subunit derivatives, in order to avoid the need for chromatographic purification prior to activation.

As described below and in the comparative Examples, protecting groups reported in the literature for doubly protected guanosines, as used for nucleic acid synthesis, did not adequately meet these criteria. Thus, a new protecting strategy was required for morpholino G subunits. As described below, use of the 4-(pivaloyloxy)benzyloxy group at O6 was found to meet all of the above criteria.

A. O6 Protecting Groups: Comparative Data

A1. 4-nitrophenethyl ether (NPE)

Figure 2:
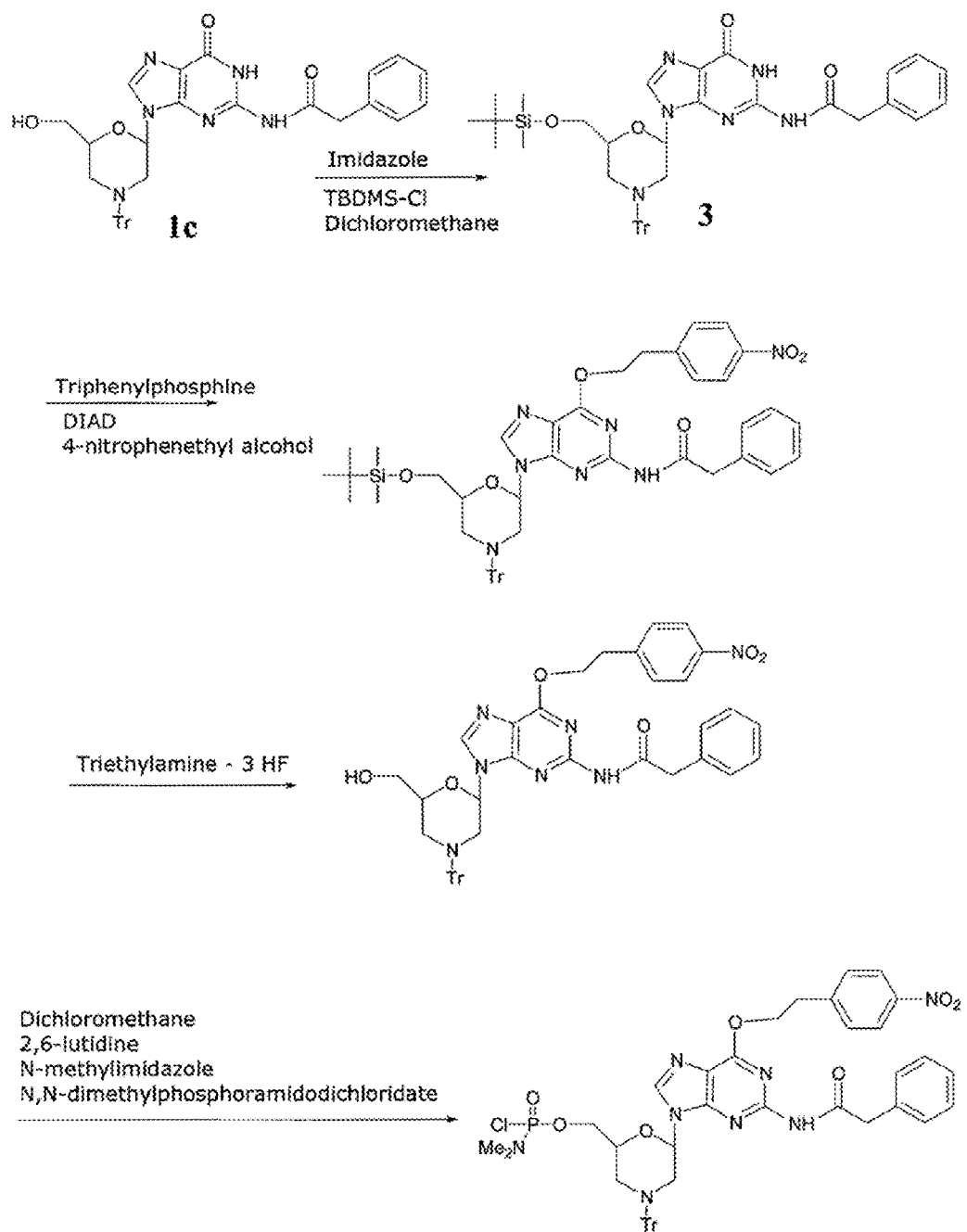
FIG. 2 illustrates a route of formation for a doubly protected morpholino G subunit (DPG) derivative in which the N2 position is phenylacetylated and the O6 position is protected with the 4-nitrophenethyl (NPE) group.
Figure 3:
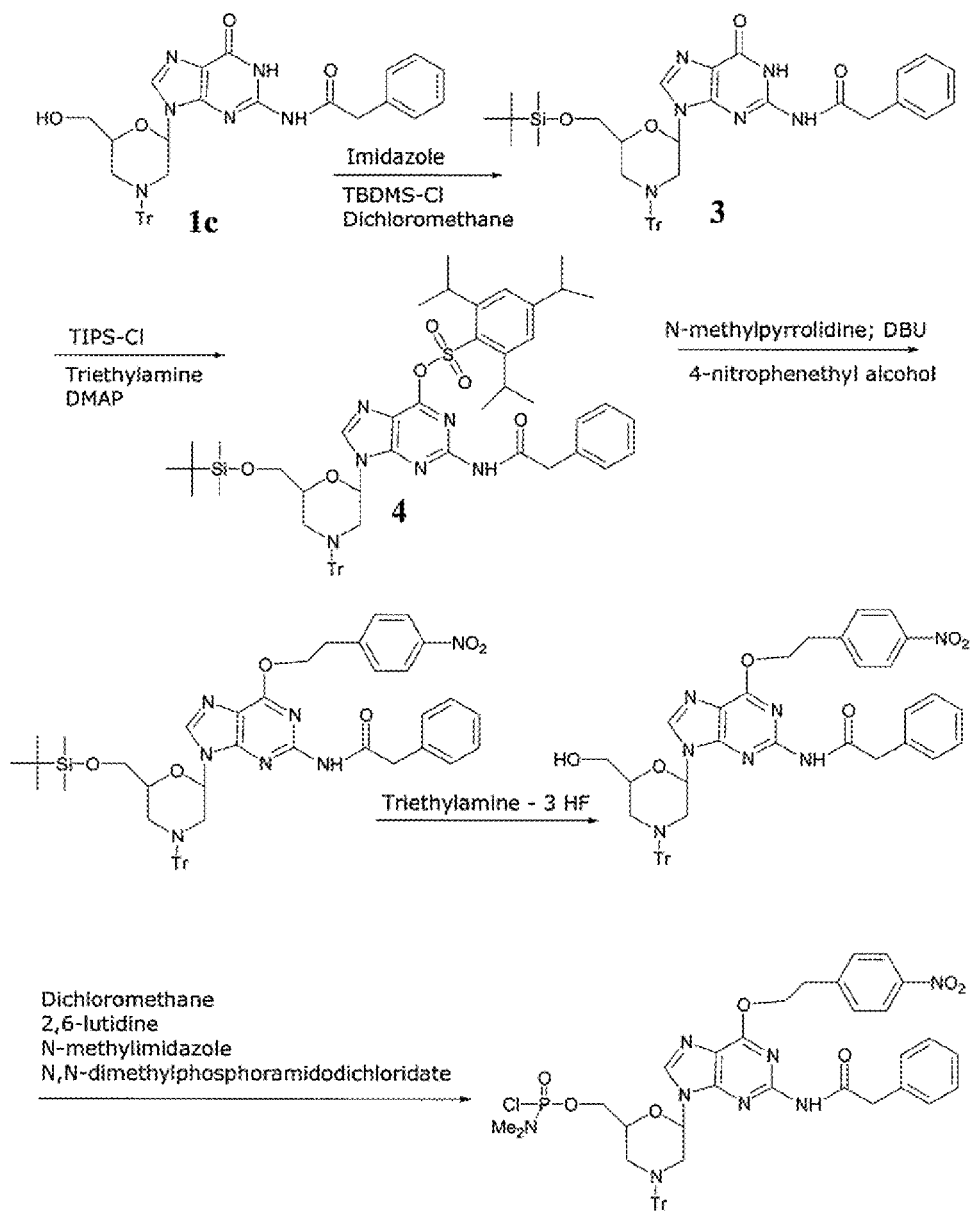
FIG. 3 illustrates an alternate route of formation for a doubly protected morpholino G subunit (DPG) derivative in which the N2 position is phenylacetylated and the O6 position is protected with the 4-nitrophenethyl (NPE) group.

This derivative was prepared as shown in FIG. 2 (Mitsunobu 1981) or FIG. 3 (Jones et al. 1982B). While the crude O6 protected subunit could be prepared in reasonable yield, the compound was not readily crystalline and could be adequately purified only by silica gel chromatography, which is undesirable for large-scale production. After testing an extensive range of reslurrying and/or recrystallization conditions, it was found that butoxyethanol-containing solvent combinations could, with some difficulty, crystallize the material. However, excess butoxyethanol could not be removed from the final product, as the compound likely crystallized as a solvate. The presence of excess alcoholic solvent would not be acceptable in the activation reaction.

The NPE group is cleaved with strong base via a β-elimination mechanism. These conditions tend to generate the reactive by-product 4-nitrostyrene, which can then react with reactive sites on the oligomer. While various scavenging agents (e.g. thiols and 1,3-dicarbonyl compounds) were introduced into the deprotection mixture in an attempt to prevent trapping of the by-product by the oligomer, none were completely successful in eliminating this internal return problem. Even after purification, oligomers prepared with this subunit had a yellow tint.

A2. Phenylsulfonylethyl (PSE) and Methylsulfonylethyl (MSE)

Figure 4:
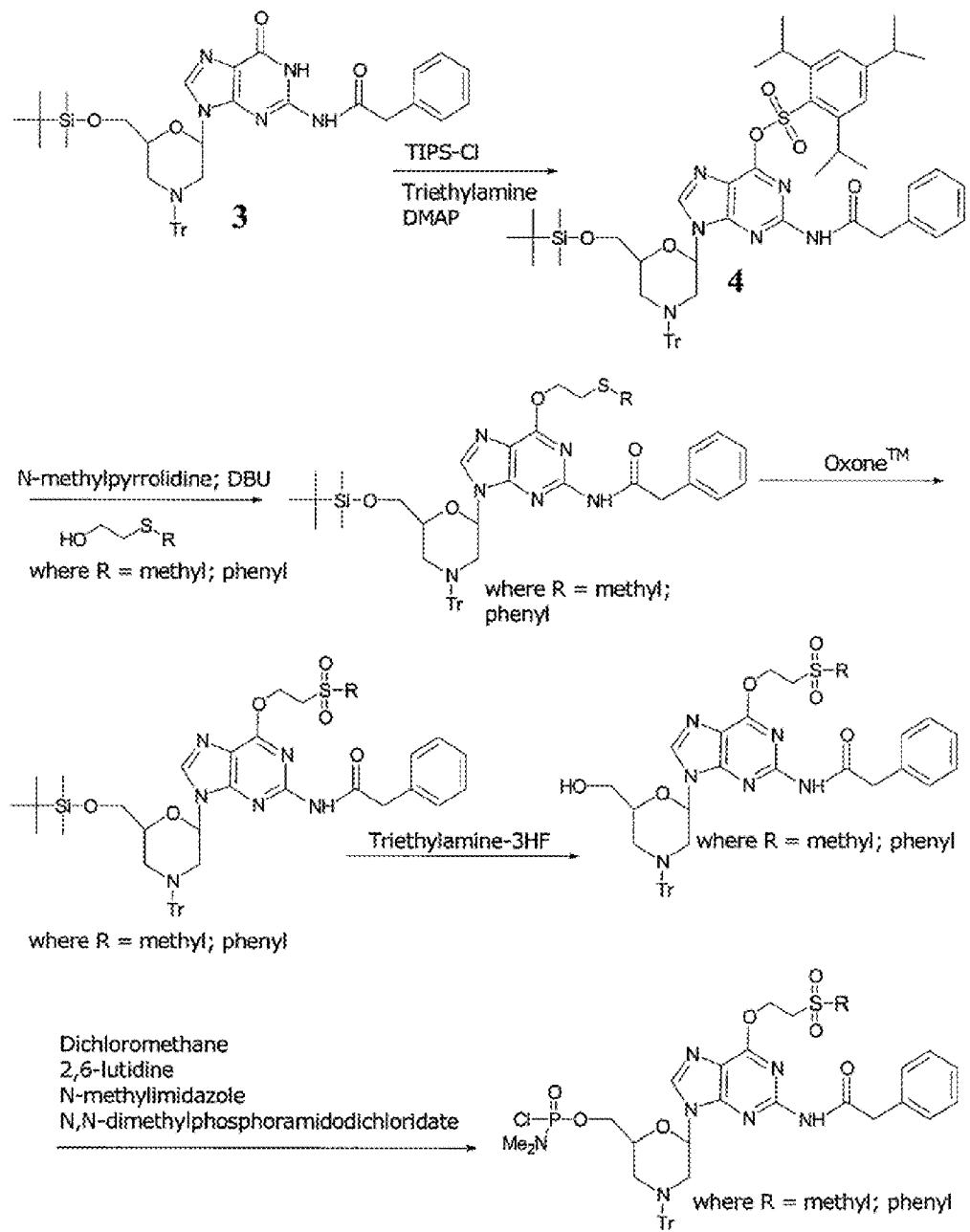
FIG. 4 illustrates the formation of a DPG derivative in which the N2 position is phenylacetylated and the O6 position is protected with either the phenylsulfonylethyl (PSE) or methylsulfonylethyl (MSE) group.

These groups were introduced via the corresponding 2-thioethanol derivatives (Jones et al. 1982A, 1982B), as shown in FIG. 4. However, no successful crystallization procedure could be found for the resulting subunits.

Like the NPE group, above, these groups are cleaved via a β-elimination mechanism. After incorporation into an oligomer, these derivatives gave the same problems seen with the NPE group; that is, internal return of the reactive alkene by-product formed during deprotection.

A3. Trimethylsilylethyl ether

Figure 5:
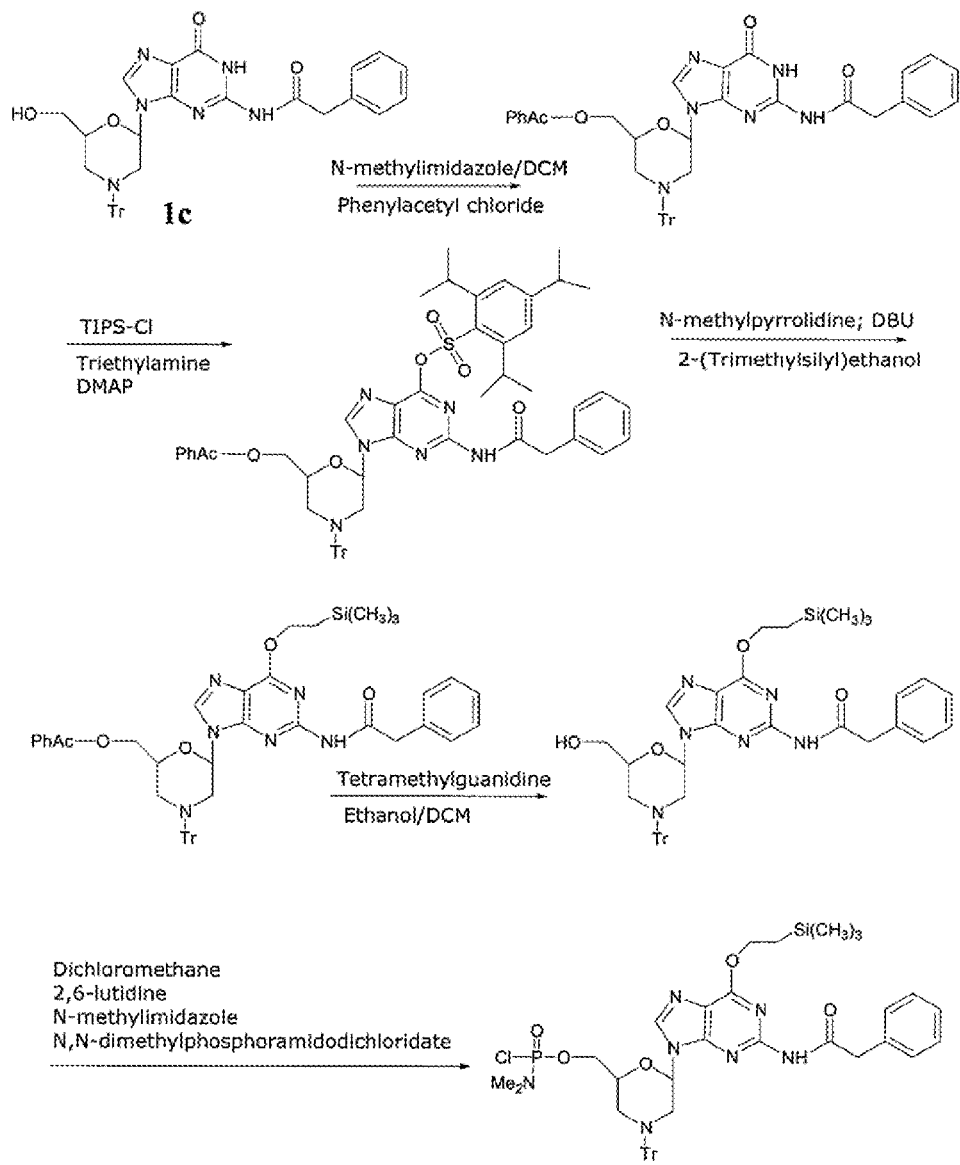
FIG. 5 illustrates the formation of a DPG derivative in which the N2 position is phenylacetylated and the O6 position is protected with the trimethylsilylethyl (TMSE) group.

As reported by Jones (Jones et al. 1982B), an O6-TMSE-modified morpholino guanine subunit was prepared as shown in FIG. 5, but it was not stable during oligomer synthesis. Oligomers made with this subunit showed a range of by-products similar to those made from O6-unprotected G subunits.

A4. Phenyl ether

Figure 6:
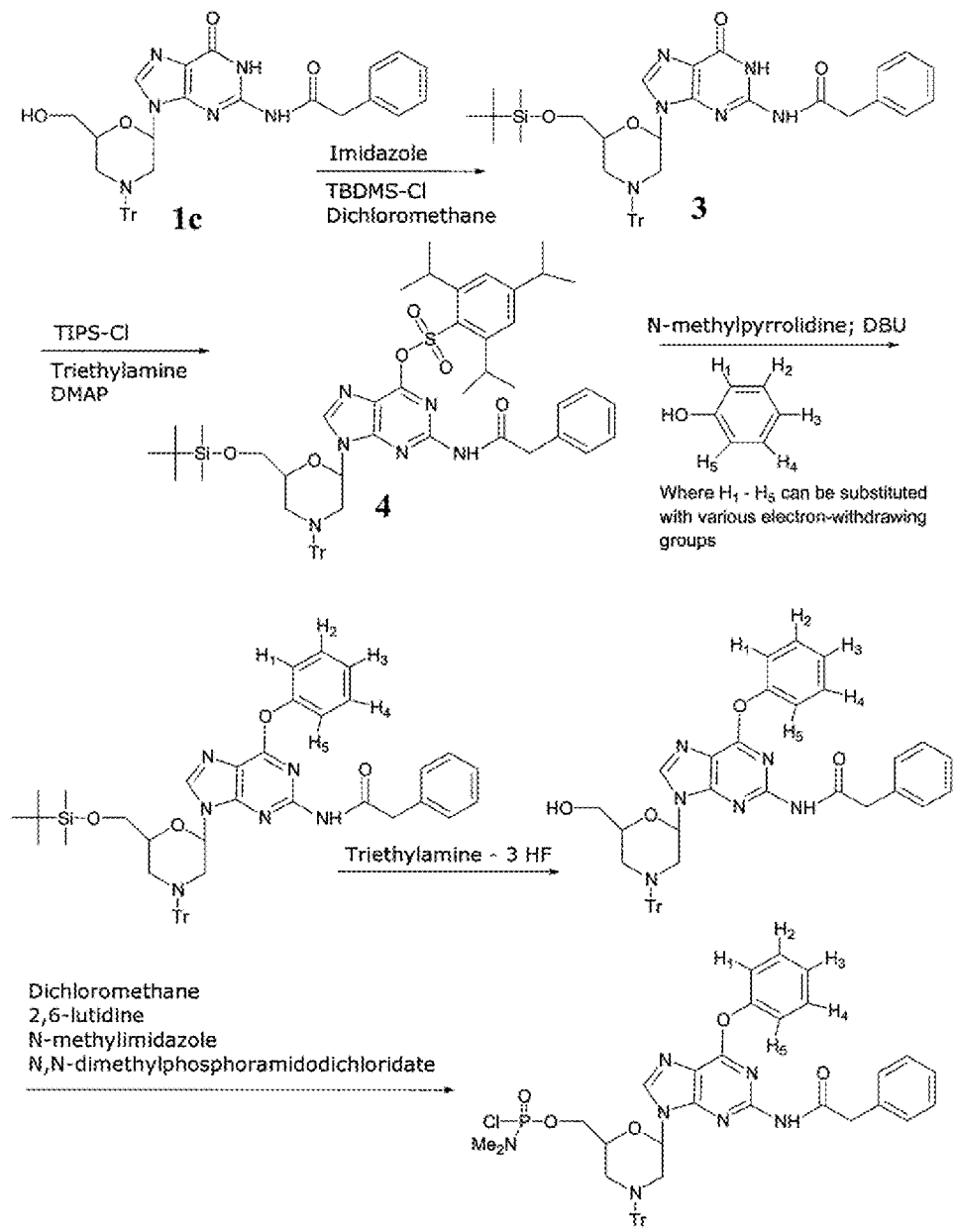
FIG. 6 illustrates the formation of a DPG derivative in which the N2 position is phenylacetylated and the O6 position is protected with a series of aryl derivatives.

Morpholino guanine subunits with O6-phenyl substitution (FIG. 6) were prepared according to the procedure of Reese et al. (1981, 1984). The derivatives included unsubstituted phenyl, 2,5-dichlorophenyl, pentafluorophenyl, and 3-fluorophenyl. Such subunits could be incorporated into PMO, but deprotection with the usual reagents, such as 2-nitrobenzaldehyde oxime and strong base, could not be carried to completion without degradation of the oligomer.

A5. Carbamate

Figure 7:
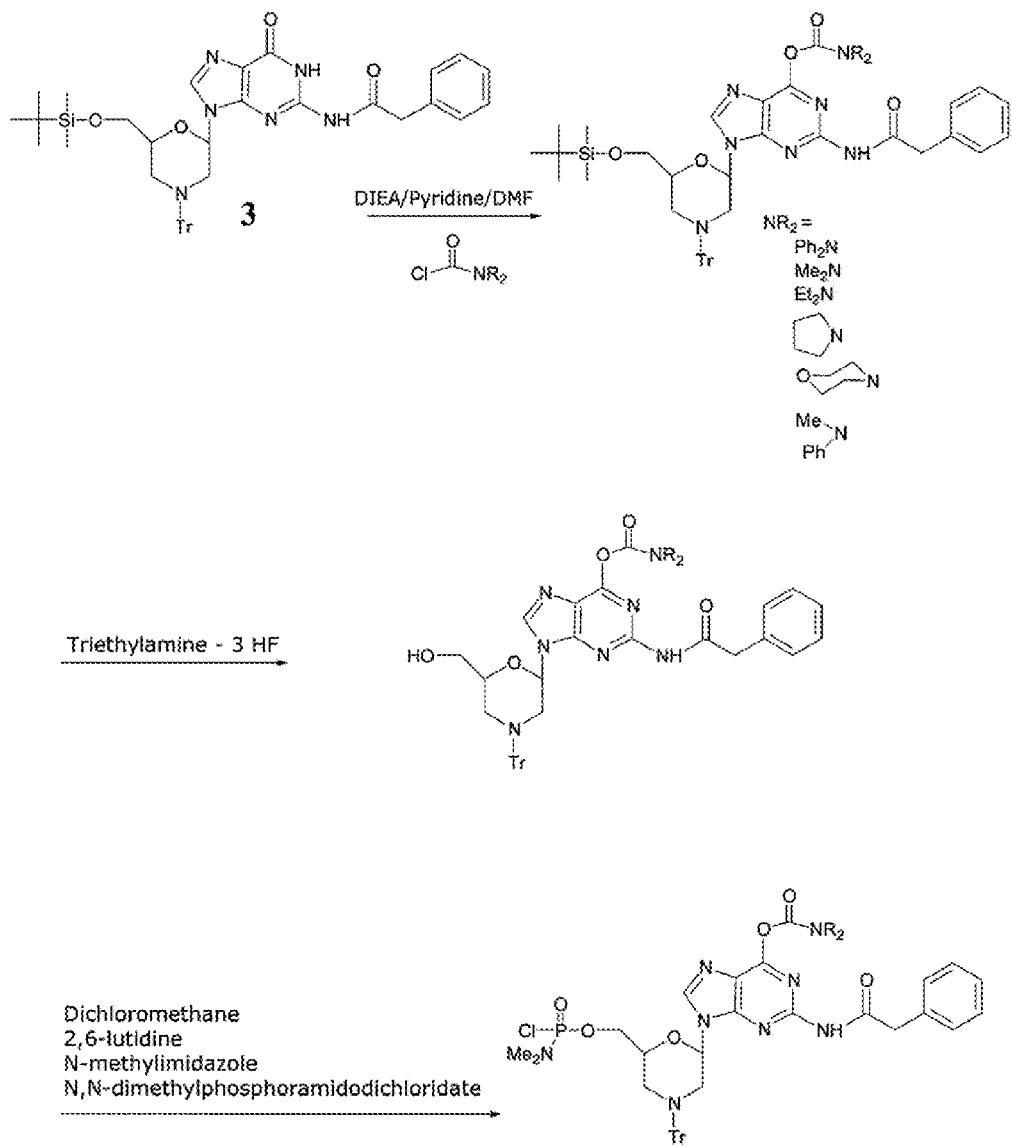
FIG. 7 illustrates the formation of a DPG derivative in which the N2 position is phenylacetylated and the O6 position is protected with a series of carbamoyl derivatives.

Several O6-carbamate derivatives were synthesized, according to the procedure of Hata et al. 1983 (FIG. 7). Use of these derivatives in oligomer synthesis gave varying results depending on the derivative used. For the more labile species, such as the diphenyl carbamoyl analog, transfer of the protecting group to the 3'-nitrogen of the growing chain was noted during the coupling step of solid phase synthesis, resulting in truncated oligomers containing a 3'-diphenylcarbamoyl moiety. In addition, the O6-carbamates have two possible sites of reaction with ammonia. While the more reactive moieties such as the diphenylcarbamoyl group gave relatively selective attack at the carbonyl, the more stable dimethyl and pyrrolidinyl carbamates showed significant competing reaction of ammonia at the C6 position, with conversion to diaminopurine.

B. 4-(Pivaloyloxy)benzyloxy Protecting Group 4-(Pivaloyloxy)benzyloxy alcohol (4a, FIG. 8) was introduced into the morpholino guanine subunit via an efficient, high-yielding synthesis. The subunit prior to activation (compound 1f in FIGS. 1 and 8) can be synthesized and reproducibly isolated at large scale without chromatographic purification, and it can be crystallized from a variety of solvents (e.g. THF/water, THF/heptane, acetonitrile, various ester/hydrocarbon mixtures). Ten batches of this subunit made at the 50-200 gallon scale (batch size: 8-27 kg of compound 1c) gave an average yield of 65% of product, having a purity (by HPLC) of 97.6% to 99.2%.

The subunit is converted to activated subunit (i.e., conversion to the 5'-chlorophosphoramidate compound) much more cleanly than mono-protected G, and it can be more easily purified by silica gel chromatography. At scale, overall yield from compound 1f to compound 2f (FIG. 1) is approximately 50%.

Figure 8:
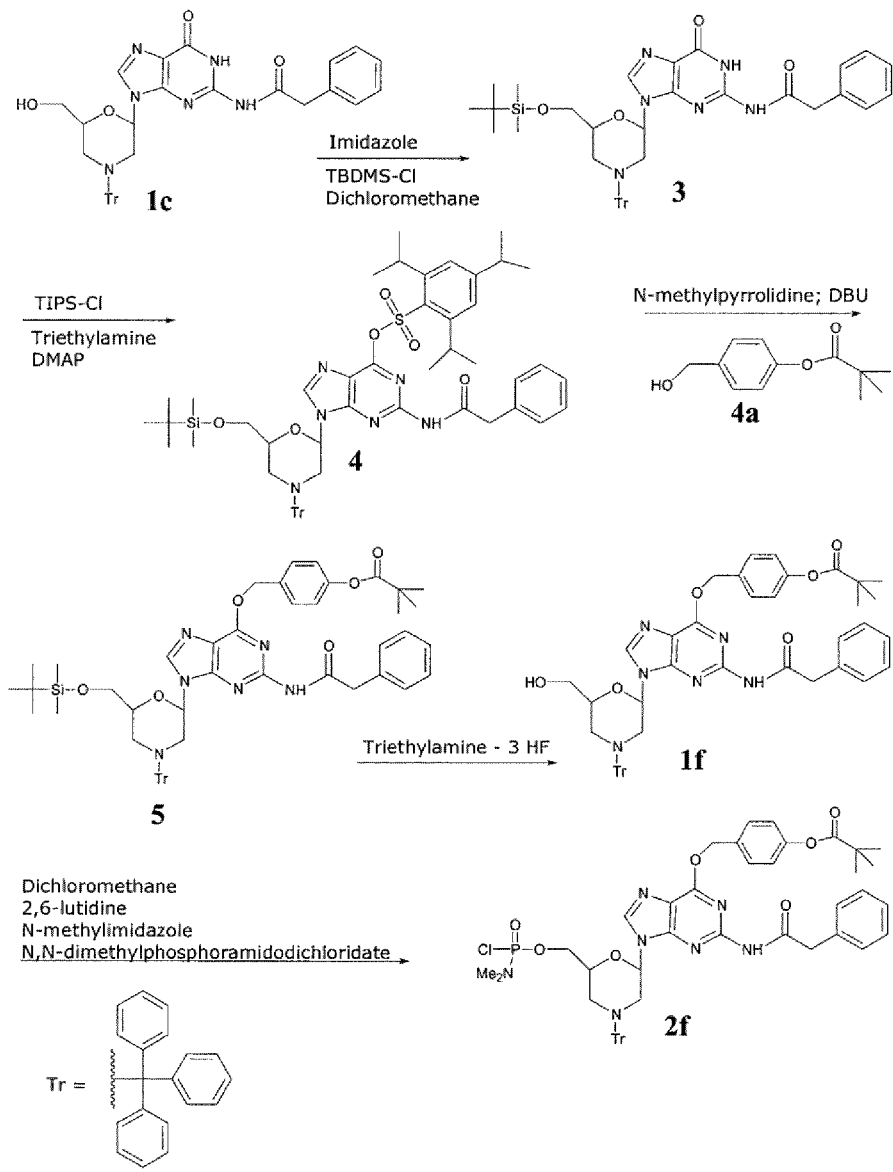
FIG. 8 illustrates the formation of the DPG derivative in which the N2 position is phenylacetylated and the O6 position is protected with the 4-(pivaloyloxy)benzyloxy (POB) group.

The POB protecting group may be employed with other combinations of protecting groups for the N2 and morpholino ring nitrogens. Suitable N2 protecting groups include phenylacetyl (as illustrated in FIG. 8) as well as acetyl, propionyl, isobutyryl, and phenoxyacetyl. Trityl species suitable for morpholino ring nitrogen protection between coupling steps include unsubstituted trityl, 4-methyl-, 4,4'-dimethyl-, and 4,4',4"-trimethyltrityl, and 4-methoxytrityl.

Other acyl protecting groups can also be used in place of pivaloyl for the phenol moiety of the POB group. Suitable alternatives include N,N-dimethylcarbamoyl and benzoyl.

During PMO synthesis, no products are seen wherein the pivaloyl group has become attached to the 3'-terminus of smaller fragments of the full length PMO, a side reaction common to the O6-carbamates discussed above. The only notable side product detected was a PMO containing a phenolic residue, resulting from reaction with the deprotection by-product quinone methide. However, this by-product could be reduced to trace levels by sufficient dilution of the ammoniacal deprotection solution. In addition, it is easily removed by virtue of strong binding of the phenolic residue to the polymeric resins used for strong anion exchange chromatography. In general, the overall yield of purified PMO is greatly increased, as seen in Table 1.

The improvement in PMO production fostered by the POB protected guanine group is most evident in the purification following PMO solid phase synthesis, where the difficulty in removing diaminopurine and related byproducts can lead to severe loss during strong anion exchange (SAX) chromatography. For example, crude purities for AVI-4126 prepared with CPM and MPG (mono-protected guanine subunit, 2c) are in the 68-73% range, which calculates to approximately 58% crude yield of the PMO. During the Trityl-On and Trityl-Off purifications, significant material is lost to obtain pure product, and the overall recovery from the chromatography is 52%. For the AVI-4126 made using CYTFA and DPG (di-protected guanine subunit), the crude purities are 70-75%, with comparable N−1 levels by mass spectrometry (indicating that detritylation efficiencies of CYTFA and CPM reagents are approximately equivalent) and crude yields of about 61%. However, application of the usual purification methods recovers 80% of the PMO from the crude mixture.

TABLE 1

| PMO AVI- | SEQ ID NO: | Sequence | Detritylation reagent[1] | Guanine Monomer | Scale[2] | Yield |
|---|---|---|---|---|---|---|
| 4126 | 1 | ACGTTGAGGGGCATCGTCGC | CAA | 2c | 54 g[3] | 18% |
| 4557 | 2 | CTGGGATGAGAGCCATCACT | CAA | 2c | 24 g[4] | 18% |
| " | " | " | CAA | 2c | 48 g[5] | 15% |
| 4126 | 1 | ACGTTGAGGGGCATCGTCGC | CPM | 2c | 25 g | 25% |
| " | " | " | CPM | 2c | 25 g | 27% |
| " | " | " | CPM | 2c | 25 g | 30% |

TABLE 1-continued

| PMO AVI- | SEQ ID NO: | Sequence | Detritylation reagent[1] | Guanine Monomer | Scale[2] | Yield |
|---|---|---|---|---|---|---|
| 4020 | 3 | CTTAGTCATCGAGATCTTCGTG | CPM | 2c | 30 g | 32% |
| 4126 | 1 | ACGTTGAGGGGCATCGTCGC | CYTFA | 2f | 25 g | 49% |
| 4065 | 4 | GTGCTCATGGTGCACGGTC[6] | CYTFA | 2f | 120 g | 46% |
| " | " | " | CYTFA | 2f | 120 g | 49% |
| " | " | " | CYTFA | 2f | 120 g | 50% |

Syntheses were performed in accordance with methods described in co-owned U.S. application Ser. No. 11/801,885, using the modifications indicated in the table; see Examples 2-5 below. All PMO have a 5'-"tail" and are unsubstituted at the 3'-terminus.

1. CAA=11% Cyanoacetic acid (w/w) in a mixture of 20% acetonitrile/DCM (v/v), CPM=2% 3-Chloropyridinum methanesulfonate (w/v) and 0.9% ethanol (v/v) in 20% trifluoroethanol/DCM (v/v), CYTFA=2% 3-Cyanopyridinum trifluoroacetate (w/v) and 0.9% ethanol (v/v) in 20% trifluoroethanol/DCM (v/v).
2. Scale is weight of starting resin in grams. Resin loading is 480-520 micromoles/g
3. Combined output of 4×12 g and 1×8 g runs.
4. Combined output of 2×12 g runs.
5. Combined output of 4×12 g runs.
6. Addition of the final C subunit was performed with an activated morpholino C subunit with 4-methoxytrityl protection on the morpholino nitrogen.

Thus, the invention provides a method of synthesizing a morpholino oligomer in increased purified yield relative to prior art methods, and particularly in comparison to purified yields observed when a monoprotected MoG monomer, or other protected MoG monomer not of the invention, is employed. In particular, the method preferably generates a reduced level of diaminopurine species than would be obtained using a MoG monomer not of the invention.

III. Doubly Protected Guanine Morpholino Subunits

The doubly protected guanine (DPG) morpholino subunits of the invention have the structure I:

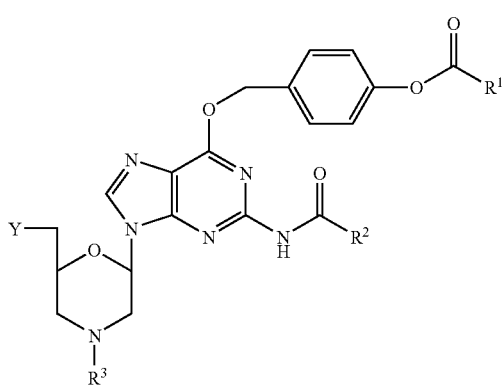

where
$R^1$ is selected from the group consisting of lower alkyl, di(lower alkyl)amino, and phenyl;
$R^2$ is selected from the group consisting of lower alkyl, monocyclic arylmethyl, and monocyclic (aryloxy)methyl;
$R^3$ is selected from the group consisting of triarylmethyl and hydrogen; and Y is selected from the group consisting of: a protected or unprotected hydroxyl or amino group; a chlorophosphoramidate group; and a phosphorodiamidate linkage to the ring nitrogen of a further morpholino compound or a morpholino oligomer.

In selected embodiments, Y is a protected or unprotected hydroxyl group (as in the pre-activated monomer) or a chlorophosphoramidate group (as in the activated monomer). Preferred protecting groups for the hydroxyl group include trialkylsilyl groups, such as tert-butyldimethylsilyl (TBDMS).

Embodiments in which Y is a phosphorodiamidate linkage to the ring nitrogen of a further morpholino compound, or a phosphorodiamidate linkage to a morpholino oligomer, refer to species formed during the synthesis of a morpholino oligomer, prior to base deprotection.

As discussed below, the substituents on the chlorophosphoramidate group (in the activated monomer) can vary depending on the specific phosphorodiamidate linkage desired.

The invention also provides, correspondingly, a method of synthesizing a morpholino oligomer, the method comprising:

(a) reacting a solid-phase-supported morpholino subunit, having an unprotected ring nitrogen, with a base-protected morpholino subunit monomer, having a triarylmethyl-protected ring nitrogen and an activated phosphoramidate group on a 5'-exocyclic carbon, thereby forming a phosphorodiamidate linkage between said 5'-exocyclic carbon and said unprotected ring nitrogen;

(b) deprotecting said protected ring nitrogen, to form an unprotected ring nitrogen; and (c) repeating steps (a) and (b) one or more times with further base-protected morpholino subunit monomers;

wherein at least one of said base-protected morpholino subunit monomers is a doubly protected guanine morpholino compound having the structure I:

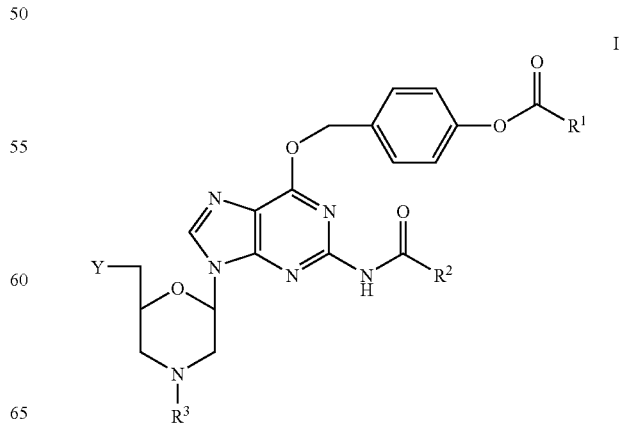

wherein

R¹ is selected from the group consisting of lower alkyl, di(lower alkyl)amino, and phenyl;

R² is selected from the group consisting of lower alkyl, monocyclic arylmethyl, and monocyclic (aryloxy)methyl;

R³ is selected from the group consisting of triarylmethyl and hydrogen; and

Y is a chlorophosphoramidate group.

Preferred triarylmethyl protecting groups for the morpholino ring nitrogen (R³) include trityl (triphenylmethyl), 4-methoxytrityl, 4-methyltrityl, 4,4'-dimethyltrityl, and 4,4',4"-trimethyltrityl.

The R¹ substituent on the 06 protecting group is preferably $C_1$ to $C_4$ alkyl, especially —C(CH₃)₃ (tert-butyl), as in the 4-(pivaloyloxy)benzyloxy (POB) group. However, R¹ can also be di(lower alkyl)amino, such as dimethylamino, or phenyl.

As noted above, substitution of the chlorophosphoramidate group Y in "activated" monomers varies depending on the structure of the desired phosphorodiamidate linkage. For preparation of the "standard" uncharged PMO linkage 5'-O—P(=O)(—N(CH₃)₂)-3' (as shown in Formula II above where R is methyl), the chlorophosphoramidate group Y is 5'-O—P(=O)Cl—NR₂ (see e.g. compound 2f, FIG. 8).

As described in co-owned application having U.S. Ser. No. 11/801,885, filed May 10, 2007, which is incorporated herein by reference, advantageous properties can be obtained by preparing PMOs having cationic as well as neutral intersubunit linkages. In such oligomers, at least one intersubunit linkage between two consecutive morpholino ring structures contains a pendant cationic group. The pendant group bears a distal nitrogen atom that can bear a positive charge at neutral or near-neutral (e.g. physiological) pH.

For preparation of such linkages, the chlorophosphoramidate group Y in the subunit monomers of the invention may have one of the following structures:

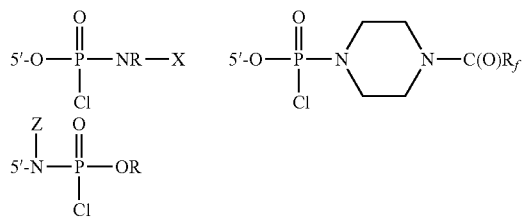

where R is lower alkyl, such as methyl or ethyl;

X=—R⁴—NHC(=O)R_f, where R⁴ is bivalent alkyl or oligo PEG, and R_f is fully or partially fluorinated methyl, ethyl, or isopropyl; and Z=X as defined above or lower alkyl. Note that the Z-containing group results in a 5'-amine containing linkage.

The term "oligo PEG" refers to a group such as —(CH₂—CH₂—O)_n—CH₂—CH₂—, where n is typically 1 to 3, and "bivalent alkyl" is typically $C_2$ to $C_8$ alkyl.

Following preparation of oligomers using monomers having such activated chlorophosphoramidate groups, the C(=O)R_f protecting groups are removed from the terminal nitrogen atoms, which may be further modified, e.g. to form terminal guanidinyl groups, as described in co-owned application U.S. Ser. No. 11/801,885.

EXAMPLES

Example 1

Synthesis of N2-PhAc, O6-POB Doubly Protected Morpholino G (DPG) Subunit (See FIG. 8)

Preparation of 3 (Starting with 35 kg of 1c): A 100 G reactor is charged with 1c (35 kg; 1.0 eq), imidazole (5.0 kg; 1.3 eq) and dichloromethane (279 kg). The batch is cooled to 3° C. A 50 G reactor is cooled to 3° C. and charged with t-butylchlorodimethylsilane (10.1 kg; 1.2 eq) and dichloromethane (93 kg). The solution in the 50 G reactor is transferred to the 100 G reactor, and the batch is adjusted to 20° C. Upon reaction completion (1-3 hours), methanol (1.8 kg; 1.0 eq) is charged to the 100 G reactor. After 30 minutes, the solution in the 100 G reactor is charged to a 200 G reactor containing pH 3 citrate buffer (376 kg of 1 M citric acid adjusted to pH 3 with solid NaOH). The batch is agitated for 30 minutes, and the layers are separated. The lower organic layer is washed once more with pH 3 citrate buffer, and once with brine solution (287 kg of 2.5% NaCl/water (w:w)). The resulting organic solution is distilled at <35° C. until Karl Fischer analysis of the batch shows <0.05% water. This solution is cooled to 3° C. in the 100 G reactor and is used directly in the preparation of compound 4.

Preparation of 4: The 100 G reactor containing the solution of compound 3 is charged with triethylamine (6.8 kg; 1.2 eq), 4-dimethylaminopyridine (0.68 kg; 0.1 eq), and triisopropylbenzenesulfonyl chloride (18.6 kg; 1.1 eq). The batch is warmed to 20° C. Upon reaction completion (3-9 hours), the solution is charged to a 200 G reactor containing pH 4.5 phosphate buffer (228 kg of 1 M KH₂PO₄). The batch is agitated for 30 minutes, and the layers are separated. The lower organic layer is washed with brine (212 kg of 2.5% NaCl/water (w:w)). The resulting organic solution is distilled at <35° C. until Karl Fischer analysis of the batch shows <0.01% water. This solution is cooled to 3° C. in the 100 G reactor and is used directly in the preparation of compound 5.

Preparation of 4a (Starting with 60 kg of 4-hydroxybenzaldehyde): A 750 G reactor is charged with 4-hydroxybenzaldehyde (60 kg; 1.0 eq), toluene (260 kg), and 1-methylimidazole (8.1 kg; 0.2 eq). To this solution is charged a solution of potassium bicarbonate (100 kg; 2.0 eq) in water (400 kg), followed by trimethylacetyl chloride (83 kg; 1.4 eq). This two-phase mixture is agitated at 20° C. Upon reaction completion (1-5 hours), methanol (15.7 kg; 1.0 eq) is charged to the batch. The batch is agitated at 20° C. for 1 hour. The layers are separated. To the upper organic layer is charged water (200 kg). The batch is agitated for 30 minutes, and the layers are separated. To the upper organic layer is charged pH 4.5 phosphate buffer (16.5 kg KH₂PO₄ in 242 kg water). The batch is agitated for 30 minutes, and the layers are separated. To the upper organic layer is charged water (200 kg). The batch is agitated for 30 minutes, and the layers are separated. The upper organic layer is distilled under vacuum at <30° C. to achieve a batch volume of 200 L. THF (70 kg) is charged to the batch, and the batch is transferred to a 500 G reactor containing Pd/C (9.6 kg; 0.004 eq; 5% Pd/C, 50% wet Johnson Matthey Type A405028-5 or A570129-5). The reactor is initially pressurized to 5 psi H₂ with the agitation set at 50 rpm. Both the pressure and agitation rate are slowly increased as the reaction proceeds, to a maximum of 25 psi H₂ and 90 rpm. Upon reaction completion (8-48 hours), the batch is filtered through a pad of Celite followed by a 0.1 micron inline filter. The Celite is rinsed with toluene (20 kg). To the batch is charged pH 6.5 phosphate buffer solution (2.7 kg $KH_2PO_4$ and 2.3 kg potassium phosphate, dibasic, trihydrate in 200 kg water). The batch is agitated for 30 minutes, and the layers are separated. The upper organic layer is distilled under vacuum at <30° C. to achieve a batch volume of 140 L. Toluene (126 kg) is charged to the batch, and the batch is distilled under vacuum at <30° C. to achieve a batch volume of 140 L. The batch is adjusted to 20° C., and transferred to a 500 G reactor containing n-heptane (821 kg) and seed crystals of compound 4a (100 grams) held at 0° C. The batch is held at 0° C. for 1-2 hours. A second portion of seed crystals (100 grams) is added, and the batch is held at 0° C. for 1-2 hours. Compound 4a is isolated by filtration. Yield=70-80% from 4-hydroxybenzaldehyde.

The derivative in which the phenol moiety is protected as its N,N-dimethylcarbamate instead of the pivalate ester is made under conditions similar to 4a. In order to push to completion the reaction between 4-hydroxybenzaldehyde and dimethylcarbamoyl chloride, the reaction is performed in refluxing dichloromethane in the presence of N-methylimidazole as base and 0.2 eq DMAP as catalyst.

Preparation of 5: A 100 G reactor containing the solution of compound 4 is charged with N-methylpyrrolidine (9.5 kg; 2.0 eq dissolved in 23 kg of dichloromethane). After 10 minutes, compound 4a (14.0 kg; 1.2 eq) is added, followed by 1,8-diazabicyclo[5.4.0]undec-7-ene (10.2 kg; 1.2 eq in 23 kg dichloromethane). The batch is warmed to 20° C. Upon reaction completion (1-9 hours), the solution is diluted with 327 kg of dichloromethane and charged to a 200 G reactor containing pH 4.5 phosphate buffer (334 kg of 1 M $KH_2PO_4$). The batch is agitated for 30 minutes, and the layers are separated. The lower organic layer is washed once more with pH 4.5 phosphate buffer (111 kg of 1 M $KH_2PO_4$), then once with brine (212 kg of 2.5% NaCl/water (w:w)). The resulting organic solution is distilled at <35° C. until Karl Fischer analysis of the batch shows <0.05% water. This solution is used directly in the preparation of compound 1f.

Preparation of 1f: A 100 G reactor containing the solution of compound 5 is charged with triethylamine trihydrofluoride (18.0 kg; 2.0 eq). The batch is agitated at 20° C. Upon reaction completion (4-20 hours), the batch is charged to a 200 G reactor. The 200 G reactor is charged with $NaHCO_3$ solution (230 kg of a 5% (w:w) solution). The batch is agitated for 30 minutes, and the layers are separated. The lower organic layer is washed once more with $NaHCO_3$ solution (230 kg of a 5% (w:w) solution), then once with pH 6.5 phosphate buffer (9.3 kg $KH_2PO_4$ and 14.0 kg $K_2HPO_4$ in 215 kg water). The resulting organic solution undergoes solvent exchange to THF (to achieve <1% DCM by weight in the batch). The solution is diluted with THF (124 kg) and heated to 60° C. Water (8 kg per kg of compound 1f in solution based on LOE analysis; pre-heated to 60° C.) is charged slowly to the THF solution. The solution is slowly cooled to 3° C. and held for >4 hours. Crude compound 1f is isolated by filtration. The crude material is re-dissolved in THF (342 kg) and heated to 60° C. Water (315 kg; pre-heated to 60° C.) is charged slowly to the THF solution. The solution is cooled to 3° C. and held for >4 hours. Compound 1f is isolated by filtration. A second recrystallization can be performed to further purify compound 1f if desired. Yield=53-73% from 1c.

Preparation of 2f (Starting with 12 kg of 1f): A 50 G reactor is charged with compound 1f (12 kg; 1.0 eq), dichloromethane (159 kg), 2,6-lutidine (2.5 kg; 1.6 eq) and 1-methylimidazole (0.36 kg; 0.3 eq). This solution is distilled to achieve a batch volume of 69 L, and cooled to 5° C. N,N-Dimethylphosphoramidodichloridate (3.8 kg; 1.6 eq) is charged to the batch. The batch is adjusted to 20° C. Upon reaction completion (6-16 hours), toluene (78 kg) is charged to the batch. The resulting mixture is distilled at 25° C. to achieve a batch volume of 126 L (GC analysis of the batch must show 30-45% DCM by weight), and transferred to a 100 G reactor containing pH 3 citrate buffer (15.4 kg citric acid monohydrate, 1.4 kg NaOH, 80 kg water). The batch is agitated for 10 minutes, and the layers are separated. The lower aqueous layer is sent to waste. The upper organic layer is transferred to the 50 G reactor containing sodium sulfate (8.0 kg). The batch is agitated for 30 minutes, and the sodium sulfate waste cake is removed by filtration. The sodium sulfate cake is rinsed with dichloromethane (16 kg). The resulting product solution is distilled in the 50 G reactor to achieve a batch volume of 53 L (GC analysis of the batch must show 11-15% DCM by weight). The 100 G reactor is charged with heptane (238 kg). The batch in the 50 G reactor is transferred to the 100 G reactor over 2 hours. At the end of the transfer, the batch is held at 20° C. for 4-16 hours. The crude compound 6 is collected by filtration. The crude material is charged to the 100 G reactor. To the crude solids is added a solution of toluene (16 kg) and heptane (50 kg). This mixture is agitated for 3 hours and filtered. The reslurry is repeated one or more times. Yield of crude 2f=80% from 1f.

Purification of Compound 2f by Silica Gel Chromatography (Starting with ~6.5 kg of crude compound 2f): The "strength" of crude compound 2f is calculated by correcting the weight of crude material for HPLC purity and volatiles. For this purification step, 5.75 kg of material (corrected for strength) is used per injection on a 50 cm chromatography column. The 50 cm chromatography column is packed with a slurry of heptane/silica gel (51.8 kg of silica gel). The crude material is loaded onto the column as a solution in dichloromethane/2,6-lutidine (15 kg dichloromethane, 0.16 kg 2,6-lutidine). The product is eluted with a two-step gradient of 4-methyl-2-pentanone (MIBK)/heptane/2,6-lutidine (first step is 827 L of 39:61 MIBK:heptane (w:w) with 0.06% 2,6-lutidine (w:w); second step is 1343 L of 73:27 MIBK:heptane (w:w) with 0.06% 2,6-lutidine (w:w)). The approved fraction pool is concentrated via thin-film evaporation to a concentration of 150 g/L. This concentrated pool is precipitated onto 6 volumes of heptane. The purified 2f is isolated by filtration. Yield of purified 2f=50% from 1f; 65% from crude 2f.

Example 2

Figure 9:
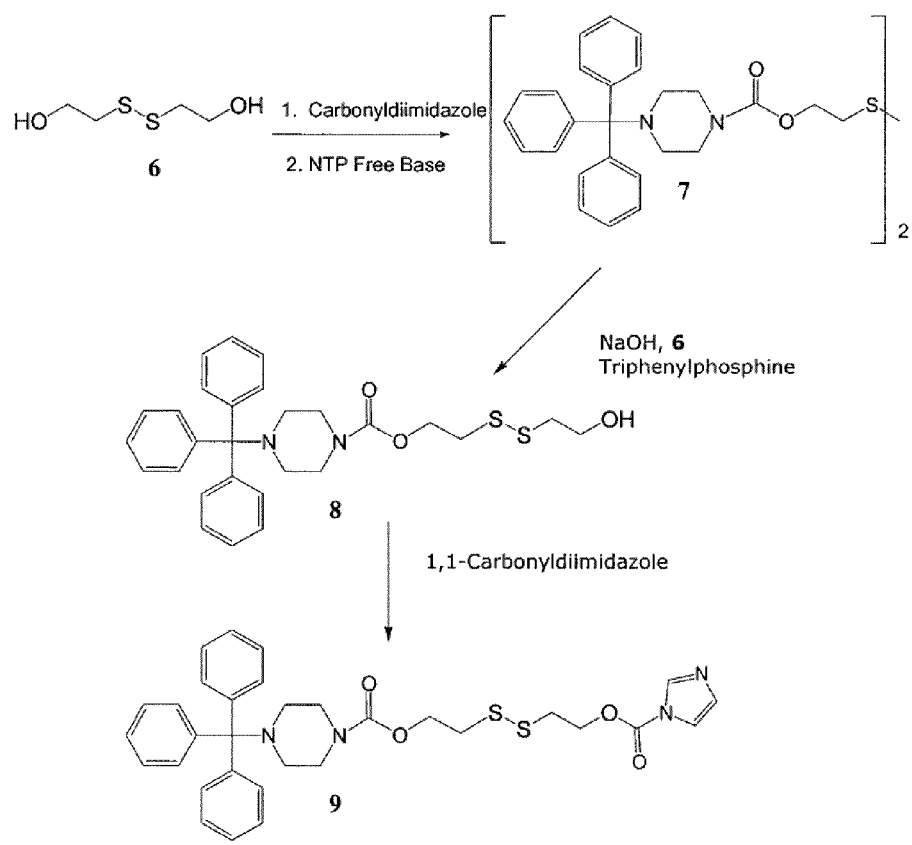
FIG. 9 illustrates the preparation of a disulfide anchor, for use in modification of a synthesis resin used for stepwise preparation of a morpholino oligomer, allowing facile release of the oligomer by treatment with a thiol.

Preparation of Disulfide Anchor (See FIG. 9)

Preparation of N-trityl piperazine, succinate salt (NTP): To a cooled solution of piperazine (10 eq) in toluene/methanol (5:1 toluene/methanol (v:v); 5 mL/g piperazine) was added slowly a solution of triphenylmethyl (trityl) chloride (1.0 eq) in toluene (5 mL/g trityl chloride). Upon reaction completion (1-2 hr), this solution was washed four times with water. To the resulting organic solution was added an aqueous solution of succinic acid (1.1 eq; 13 mL water/g succinic acid). This mixture was stirred for 90 min, and the solid product was collected by filtration. The crude NTP was purified by two reslurries in acetone. Yield=70%.

Preparation of symmetrical disulfide 7: 1,1'-Carbonyldiimidazole (CDI) (12.402 g; 2.2 eq.) was suspended in dichloromethane (5.25 mL/g) and cooled on an ice bath. Hydroxyethyl disulfide 6 (5.36 g; 1 eq.) was dissolved in dichloromethane (10 mL/g) and tetrahydrofuran (1 mL/g). The diol solution was added to the CDI slowly such that the temperature of the mixture stayed below 4° C. for the duration of the reaction. Upon reaction completion (once addition was complete), de-ionized water (93.8 μL, 0.15 eq.) was added to quench the reaction. Independently, N-trityl piperazine, succinate salt (NTP) (32.59 g; 2.1 eq.) was dissolved in toluene (8 mL/g NTP), dichloromethane (2 mL/g NTP), and methanol (2 mL/g NTP). $K_2CO_3$ (22.09 g; 4.6 eq.) was dissolved in de-ionized water (10 mL/g). The $K_2CO_3$ solution added to the solution of NTP; the mixture was stirred and then separated into two layers. The cloudy organic layer was distilled to remove 90 grams; the resulting water droplets were separated and acetone (8 mL/g NTP) was added to the organic layer. The solution of CDI activated disulfide diol was added to the solution of the free base and concentrated to 225 mL. Acetone (10 mL/g NTP) was added and the mixture was concentrated to 225 mL. The mixture was heated to reflux and solid began crystallizing out of solution. Upon completion, the reaction mixture was cooled and the solid (7) was isolated by filtration. Yield: 27.92 g; 93.1% (based on weight-based assay).

Preparation of disulfide alcohol 8: 7 (36.00 g; 32.1 mmol; 1 eq.) was suspended in acetone (2.8 mL/g 7). Hydroxyethyl disulfide (78.51 mL; 20 eq.) was added followed by acetone (1.7 mL/g 7). 5% NaOH/methanol (2.85 mL; 0.1 eq.) was added; the pH of the mixture was 10 by pH paper. Triphenylphosphine (8.42 g; 1 eq.) was added followed by acetone (1.1 mL/g 7). All solids went into solution and then product began to crystallize out. After sixteen hr, the reaction mixture was neutralized with acetic acid (2.4 g; 0.2 eq.). The crude product was isolated by filtration. The crude solid 8 was subjected to two refluxing acetone reslurries (5 mL/g 7).

After filtration the crude product was suspended in dichloromethane (7.25 mL/g 7). The mixture was heated until a clear solution formed (35° C.). The solution was extracted five times with an equal volume of de-ionized water and the final organic layer was concentrated to 155 mL. Dichloromethane was added (4.3 mL/g 7), and the solution was again concentrated to 155 mL. CDI (9.17 g; 1.1 eq.) was added and the mixture was stirred at room temperature. Upon reaction completion (~20 min) the reaction mixture was washed twice with an equal volume of de-ionized water, then ethylbenzene (2.1 mL/g 7) was added. The solution was concentrated to 65.2 g, reducing the dichloromethane in the solution to 0.17%, and stirred on an ice bath to crystallize the product. The product 9 was isolated by filtration. Yield: 44%.

Example 3

Figure 10:
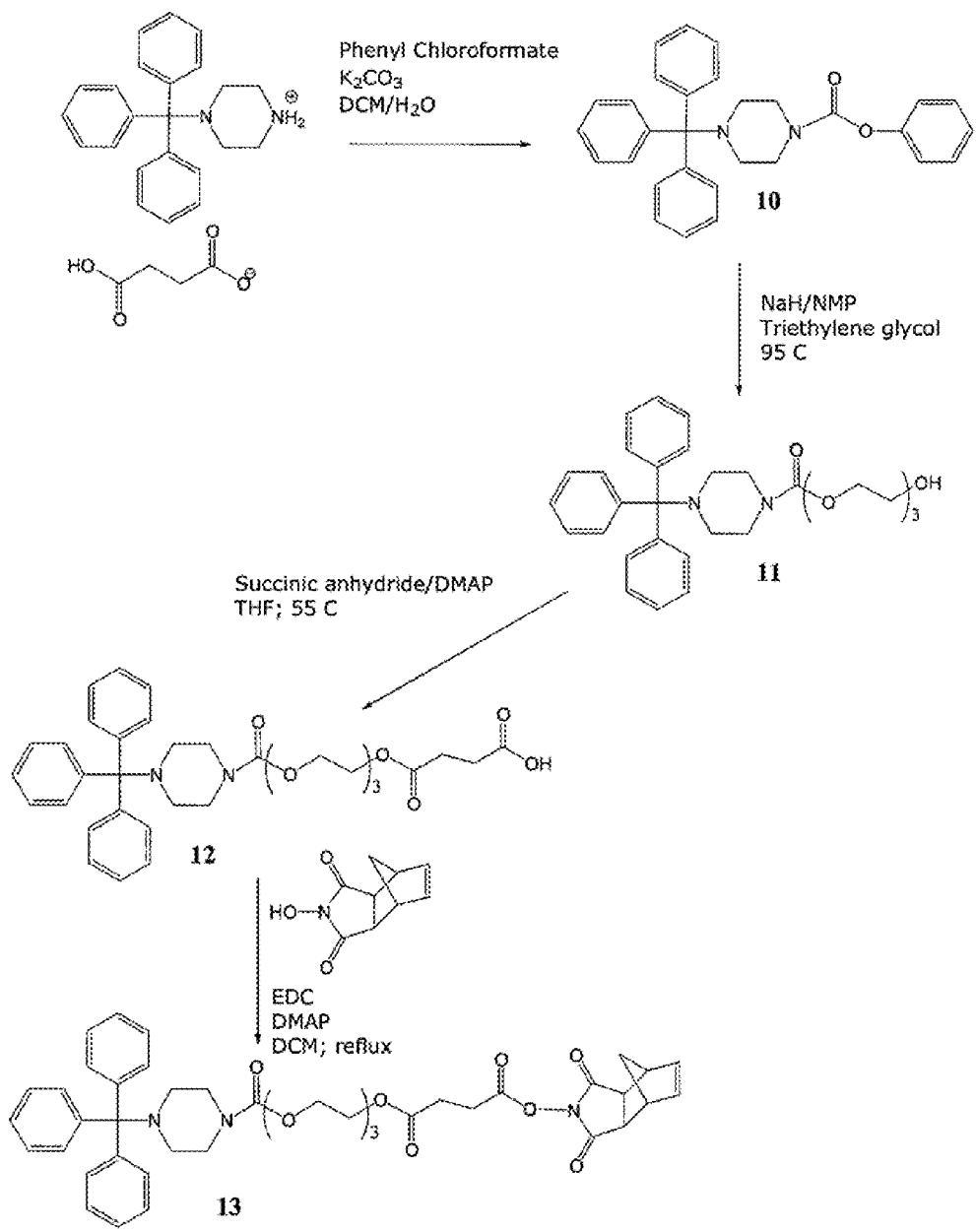
FIG. 10 illustrates the preparation of a triethylene glycol containing moiety ("Tail") which increases aqueous solubility of synthetic antisense oligomers.

Triethylene glycol Tail (See FIG. 10)

Preparation of trityl piperazine phenyl carbamate 10: To a cooled suspension of NTP in dichloromethane (6 mL/g NTP) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 10 was isolated by crystallization from acetonitrile. Yield=80%

Preparation of carbamate alcohol 11: Sodium hydride (1.2 eq) was suspended in 1-methyl-2-pyrrolidinone (32 mL/g sodium hydride). To this suspension were added triethylene glycol (10.0 eq) and compound 10 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 11 was isolated by crystallization from dichloromethane/methyl tert-butyl ether/heptane. Yield=90%.

Preparation of Tail acid 12: To a solution of compound 11 in tetrahydrofuran (7 mL/g 11) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous $NaHCO_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This DCM solution of 12 was used without isolation in the preparation of compound 13.

Preparation of 13: To the solution of compound 12 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 13 from compound 11. Introduction of the activated "Tail" onto the disulfide anchor-resin was performed in NMP by the procedure used for incorporation of the subunits during solid phase synthesis.

Example 4

Preparation of the Solid Support for Synthesis of Morpholino Oligomers

Example 4a

Preparation of Aminomethylpolystyrene-disulfide resin

This procedure was performed in a silanized, jacketed peptide vessel (custom made by ChemGlass, NJ, USA) with a coarse porosity (40-60 μm) glass frit, overhead stirrer, and 3-way Teflon stopcock to allow $N_2$ to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow $N_2$ flow up through the frit and the specified resin treatment/wash was added to the reactor and allowed to permeate and completely wet the resin. Mixing was then started and the resin slurry mixed for the specified time. For solvent/solution extraction, mixing and $N_2$ flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g $N_2$ substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 9 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 14 was dried under a $N_2$ stream for 1-3 hr and then under vacuum to constant weight (±2%). Yield: 110-150% of the original resin weight.

Example 4b

Determination of the Loading of Aminomethylpolystyrene-disulfide resin

The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient ($\epsilon$: 41 µmol$^{-1}$ cm$^{-1}$) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Example 4c

Figure 11:
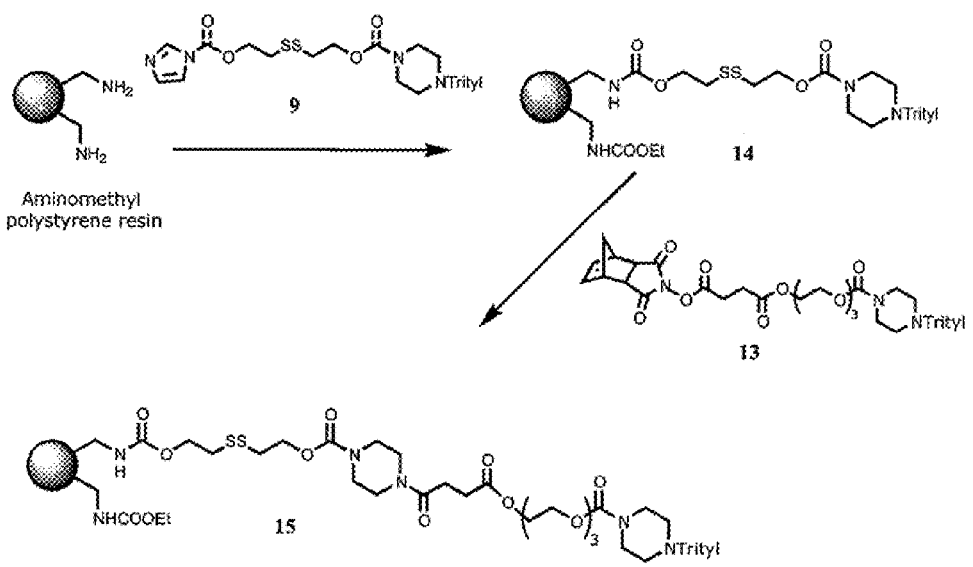
FIG. 11 illustrates the preparation of resins useful for the solid phase synthesis of morpholino oligomers.

Tail Loading (See FIG. 11)

Using the same setup and volumes as for the preparation of aminomethylpolystyrene-disulfide resin, the Tail can be introduced into the molecule. For the coupling step, a solution of 13 (0.2 M) in NMP containing 4-ethylmorpholine (NEM, 0.4 M) was used instead of the disulfide anchor solution. After 2 hr at 45° C., the resin 15 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 15 was filtered and dried under high vacuum. The loading for resin 15 is defined to be the loading of the original aminomethylpolystyrene-disulfide resin 14 used in the Tail loading.

Example 5

Synthesis of Morpholino Oligomers

Example 5a

Solid Phase Synthesis

Protected oligomers were prepared manually by solid phase oligomer synthesis on aminomethylpolystyrene-disulfide resin (~500 µmol/g loading) at 10 g scale (starting resin weight). Solutions used were as follows:

Detritylation solutions: CAA=11% Cyanoacetic acid (w/w) in a mixture of 20% acetonitrile/DCM (v/v);

CPM=2% 3-Chloropyridinum methanesulfonate (w/v) and 0.9% ethanol (v/v) in 20% trifluoroethanol/DCM (v/v);

CYTFA=2% 3-Cyanopyridinum trifluoroacetate (w/v) and 0.9% ethanol (v/v) in 20% trifluoroethanol/DCM (v/v).

Neutralization solution: 5% diisopropylethylamine in 25% isopropanol/dichloromethane;

Coupling solutions: 0.165 M (for 2f (DPG), 2c, and 2d or other T subunits) or 0.18 M (for 2a and 2b or other A/C subunits) activated Morpholino Subunit and 0.4 M N-ethylmorpholine in 1,3-dimethylimidazolidinone (DMI).

Activated MPG (2c) was prepared as in Summerton et al. (1993).

After transfer of the resin to the synthesis reactor and prior to initiating synthesis cycles, 1-methyl-2-pyrrolidinone (NMP, 20 mL/g resin) was added and allowed to sit for 1-2 hrs. After washing 2 times with dichloromethane (10 mL/g resin), the following synthesis cycle was used with addition of the appropriate coupling solution of activated Morpholino Subunit of the desired base and desired linkage type at each cycle to give the proper sequence.

| Step | Volume (mL/g of starting resin)* | Time (min) |
|---|---|---|
| DCM | 10-30 | 1-2 |
| DCM | 10-30 | 1-2 |
| Detritylation A | 10-30 | 2-3 |
| Detritylation A | 10-30 | 2-3 |
| Detritylation A | 10-30 | 2-3 |
| Detritylation A | 10-30 | 2-3 |
| Detritylation A | 10-30 | 2-3 |
| Neutralization A | 10-30 | 3-4 |
| Neutralization A | 10-30 | 3-4 |
| Neutralization A | 10-30 | 3-4 |
| Neutralization A | 10-30 | 3-4 |
| DCM | 10-30 | 1-2 |
| DCM | 10-30 | 1-2 |
| Coupling | 7-12** | 90 |
| Neutralization A | 10-30 | 1-2 |
| Neutralization A | 10-30 | 1-2 |
| Neutralization A | 10-30 | 1-2 |
| Neutralization A | 10-30 | 1-2 |
| DCM | 10-30 | 1-2 |

*Wash volumes are incremented to account for resin swelling; volume is 10 mL/g of actual resin volume at each cycle
**Coupling volumes are sufficient to maintain good mixing and are incremented to account for resin swelling After incorporation of the final subunit, a final cycle (methoxytritylation) was performed with 0.32 M 4-methoxytriphenylmethyl chloride and 0.4 M N-ethylmorpholine in DMI. After methoxytritylation, the resin was washed 8 times with NMP and then treated with cleavage solution consisting of 0.1

M 1,4-dithiothreitol (DTT) and 0.73 M triethylamine in NMP (27 mL/g starting resin) for 30 min. After collection of the protected oligomer solution, the resin (significantly reduced in volume) was washed with two additional portions of cleavage solution (13 mL/g starting resin for 15 min each) and the washes were combined with the bulk solution. To the protected oligomer solution in an appropriately sized pressure bottle with Teflon plug (Ace Glass, NJ, USA) was added concentrated aqueous ammonia (106 mL/g starting resin, previously cooled to −20° C.), the bottle sealed, and the contents mixed by swirling. The bottle was placed in a 45° C. oven for 16-20 hr to remove base and backbone protecting groups.

Following ammonolysis, the crude oligomer solution is cooled to room temperature and then diafiltered against 0.28% aqueous ammonia using a PLBC 3 kd Regenerated Cellulose membrane (Millipore) to remove solvents and small molecules prior to ion exchange chromatography.

Example 5b

Purification of Morpholino Oligomers by Anion Exchange Chromatography

The crude oligomer solution obtained from diafiltration is adjusted to pH 11-11.5 and loaded onto a column of ToyoPearl Super-Q 650S anion exchange resin (Tosoh Bioscience). The methoxytritylated oligomer is eluted with a gradient of 5-35% B over 17 column volume (Buffer A: 10 mM sodium hydroxide; Buffer B: 1 M sodium chloride in 10 mM sodium hydroxide) and fractions of acceptable purity (anion exchange HPLC and mass spec) pooled.

Example 5c

Demethoxytritylation of Morpholino Oligomers

To the pooled fractions from anion exchange chromatography is added acetonitrile (10% by volume) followed by 2 M $H_3PO_4$ to adjust the pH to 3. The solution is mixed for 45 min and then neutralized with concentrated aqueous ammonia to pH 7. The oligomer solution is diafiltered against 20 mM sodium acetate using a PLBC 3 kd Regenerated Cellulose membrane (Millipore) to exchange buffers prior to cation exchange chromatography.

Example 5d

Purification of Morpholino Oligomers by Cation Exchange Chromatography

The oligomer solution is adjusted to pH 4.5 with acetic acid and loaded onto a column of Source 30S cation exchange resin (GE Healthcare). The oligomer is eluted with a gradient of 0-35% B over 17 column volumes (Buffer A: 20 mM sodium acetate, 25% acetonitrile, pH 4.5; Buffer B: 0.5 M sodium chloride, 20 mM sodium acetate, 25% acetonitrile, pH 4.5) and fractions of acceptable purity (cation exchange HPLC and mass spec) pooled.

The invention claimed is:

1. A morpholino compound having the following structure I:

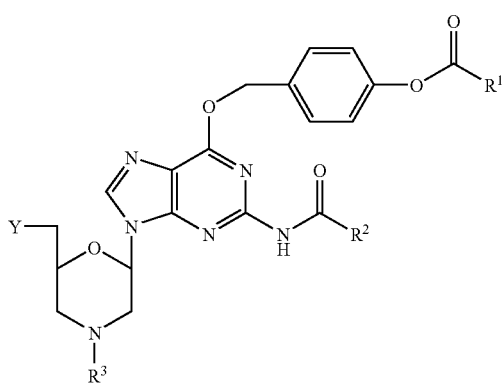

wherein:
- $R^1$ is lower alkyl, di(lower alkyl)amino or phenyl;
- $R^2$ is lower alkyl, monocyclic arylmethyl or monocyclic (aryloxy)methyl;
- $R^3$ is triarylmethyl or hydrogen; and
- Y is a protected or unprotected hydroxyl group, a protected or unprotected amino group, a chlorophosphoramidate group, a phosphorodiamidate linkage to the morpholino ring nitrogen of a morpholino subunit monomer, a phosphorodiamidate linkage to the morpholino ring nitrogen of a morpholino subunit in a morpholino oligomer or a linkage to a solid support.

2. The compound of claim 1, wherein Y is a protected or unprotected hydroxyl group or a chlorophosphoramidate group.

3. The compound of claim 2, wherein Y is a trialkylsilyl-protected hydroxyl group or an unprotected hydroxyl group.

4. The compound of claim 2, wherein Y is a chlorophosphoramidate group having the following structure:

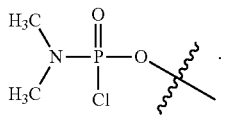

5. The compound of claim 1, wherein $R^3$ is trityl, 4-methoxytrityl, 4-methyltrityl, 4,4'-dimethyltrityl or 4,4',4''-trimethyltrityl.

6. The compound of claim 1, wherein $R^1$ is lower alkyl.

7. The compound of claim 6, wherein $R^1$ is —C(CH$_3$)$_3$.

8. The compound of claim 1, wherein $R^2$ is benzyl or —CH(CH$_3$)$_2$.

9. A method of synthesizing a morpholino oligomer, the method comprising:

(a) reacting
a solid-phase-supported morpholino subunit monomer comprising an unprotected morpholino ring nitrogen
with a first morpholino subunit monomer comprising a triarylmethyl-protected morpholino ring nitrogen and an activated phosphoramidate group on a 5'-exocyclic carbon, thereby forming a phosphorodiamidate linkage between the 5'-exocyclic carbon of the first morpholino subunit monomer and the unprotected morpholino ring nitrogen of the solid-phase-supported morpholino subunit monomer;

(b) deprotecting the triarylmethyl-protected morpholino ring nitrogen to form a product comprising an unprotected morpholino ring nitrogen;

(c) optionally reacting the product from step (b) with a further morpholino subunit monomer comprising a triarylmethyl-protected morpholino ring nitrogen and an activated phosphoramidate group on a 5'-exocyclic carbon, thereby forming a phosphorodiamidate linkage between the 5'-exocyclic carbon of the further morpholino subunit monomer and the unprotected morpholino ring nitrogen of the product from step (b); and (d) optionally repeating steps (b) and (c) one or more times;
wherein at least one of the first morpholino subunit monomer, the further morpholino subunit monomer or the solid-phase-supported morpholino subunit monomer is a doubly protected guanine morpholino compound having the following structure I:

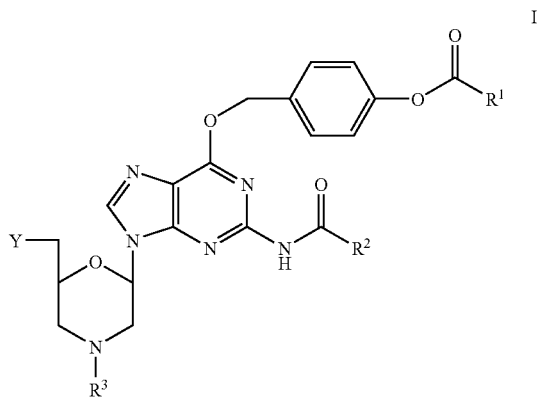

wherein:
- $R^1$ is lower alkyl, di(lower alkyl)amino or phenyl;
- $R^2$ is lower alkyl, monocyclic arylmethyl or monocyclic (aryloxy)methyl;
- $R^3$ is triarylmethyl or hydrogen; and
- Y is a chlorophosphoramidate group or a linkage to a solid support.

10. The method of claim 9, wherein Y is a chlorophosphoramidate group having the following structure:

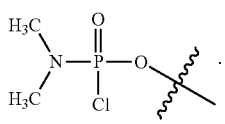

11. The method of claim 9, wherein $R^3$ is trityl, 4-methoxytrityl, 4-methyltrityl, 4,4'-dimethyltrityl or 4,4',4"-trimethyltrityl.

12. The method of claim 9, wherein $R^1$ is lower alkyl.

13. The method of claim 12, wherein $R^1$ is —C(CH$_3$)$_3$.

14. The method of claim 9, wherein $R^2$ is benzyl or —CH(CH$_3$)$_2$.

15. The compound of claim 1, wherein the compound has the following structure:

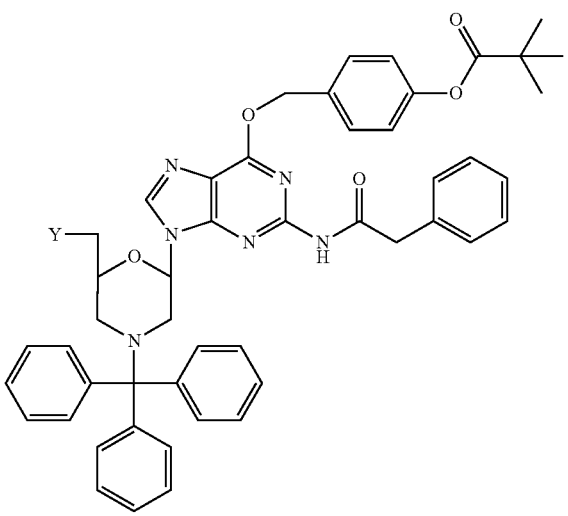

wherein Y is a linkage to a solid support or a chlorophosphoramidate group having the following structure:

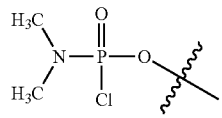

16. The method of claim 9, wherein at least one of the first morpholino subunit monomers, the further morpholino subunit monomer or the solid-phase-supported morpholino subunit monomer has the following structure:

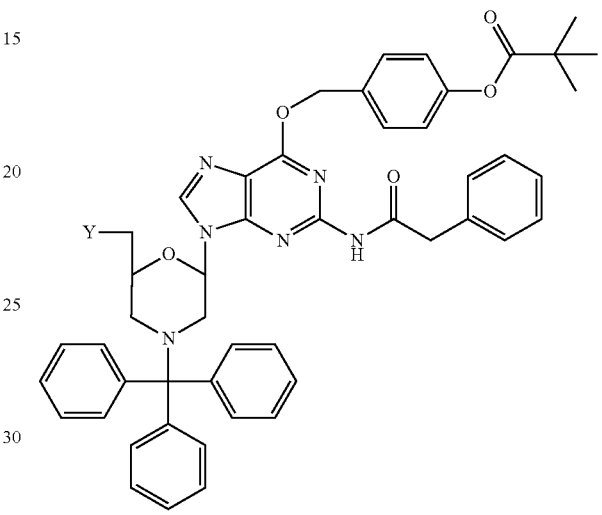

wherein Y is a linkage to a solid support or a chlorophosphoramidate group having the following structure:

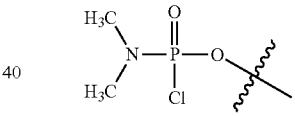

* * * * *

UNITED STATES PATENT AND TRADEMARK OFFICE
CERTIFICATE OF CORRECTION

| | | |
|---|---|---|
| PATENT NO. | : 8,076,476 B2 | Page 1 of 1 |
| APPLICATION NO. | : 12/271040 | |
| DATED | : December 13, 2011 | |
| INVENTOR(S) | : Matthew Dale Reeves et al. | |

It is certified that error appears in the above-identified patent and that said Letters Patent is hereby corrected as shown below:

In the Claims:

Column 24, Line 11:
"morpholino subunit monomers, the further morpholino" should read, --morpholino subunit monomer, the further morpholino--.

Signed and Sealed this
Fourth Day of June, 2013

Teresa Stanek Rea
*Acting Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 1
acgttgaggg gcatcgtcgc                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 2
ctgggatgag agccatcact                                                      20

<210> SEQ ID NO 3
<211> LENGTH: 22
<212> TYPE: DNA
<213> ORGANISM: Artificial Sequence
<220> FEATURE:
<223> OTHER INFORMATION: Synthetic oligomer

<400> SEQUENCE: 3
cttagtcatc gagatcttcg tg                                                   22

<210> SEQ ID NO 4
<211> LENGTH: 19
```

```
<212> TYPE: DNA
<213> ORGANISM: Artificial Sequence
<220> FEATURE:
<223> OTHER INFORMATION: Synthetic oligomer

<400> SEQUENCE: 4
gtgctcatgg tgcacggtc                                              19
```